(12) United States Patent
Dorn et al.

(10) Patent No.: US 8,589,197 B2
(45) Date of Patent: Nov. 19, 2013

(54) METHOD AND COMPUTER SYSTEM FOR ADMINISTRATION OF MEDICAL APPLICATIONS EXECUTING IN PARALLEL

(75) Inventors: Karlheinz Dorn, Kalchreuth (DE); Vladyslav Ukis, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 567 days.

(21) Appl. No.: 12/776,528

(22) Filed: May 10, 2010

(65) Prior Publication Data

US 2010/0293548 A1 Nov. 18, 2010

(30) Foreign Application Priority Data

May 12, 2009 (DE) .......................... 10 2009 020 918

(51) Int. Cl.
*G06Q 10/00* (2012.01)
(52) U.S. Cl.
USPC ........................................................ 705/7.11
(58) Field of Classification Search
USPC ........................................................ 705/7.11
See application file for complete search history.

(56) References Cited

U.S. PATENT DOCUMENTS

| 7,234,147 | B1 * | 6/2007 | Gharavy et al. | ............... | 719/318 |
| 2002/0120679 | A1 * | 8/2002 | Hayton et al. | ................ | 709/203 |
| 2002/0199025 | A1 * | 12/2002 | Kutay et al. | ................... | 709/250 |
| 2006/0206861 | A1 * | 9/2006 | Shenfield et al. | ............. | 717/106 |
| 2009/0125420 | A1 * | 5/2009 | Zhang | ............................. | 705/27 |

\* cited by examiner

*Primary Examiner* — Romain Jeanty
(74) *Attorney, Agent, or Firm* — Harness, Dickey & Pierce, P.L.C.

(57) ABSTRACT

A method and a computer system are disclosed for administration of medical applications running in parallel. At least one embodiment of the method includes creation of a number of application components as a result a beginning of a number of user actions; provision of a module for parallel execution and/or for coordination of the previously created application components, provision of a least one communication interface for exchanging messages and/or data between an application component and a command which is of interest to the application component which has been initiated by one of the user actions, and removal of the application component created by a user action after the user action has ended.

12 Claims, 1 Drawing Sheet

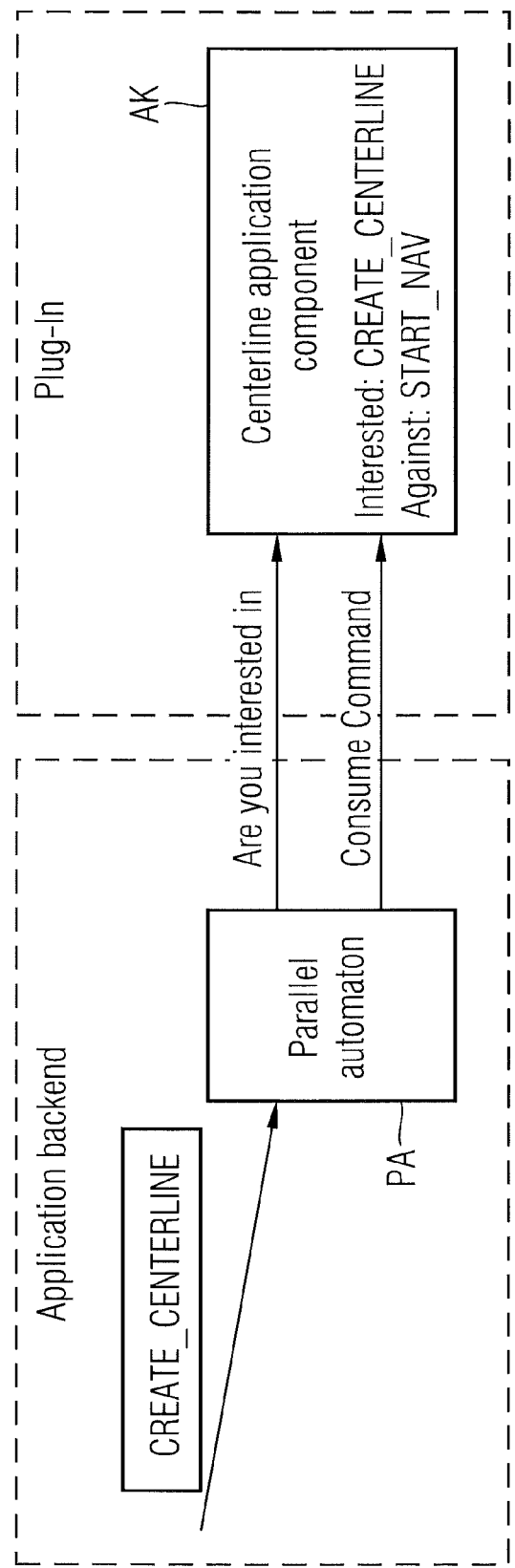

METHOD AND COMPUTER SYSTEM FOR ADMINISTRATION OF MEDICAL APPLICATIONS EXECUTING IN PARALLEL

PRIORITY STATEMENT

The present application hereby claims priority under 35 U.S.C. §119 on German patent application number DE 10 2009 020 918.2 filed May 12, 2009, the entire contents of which are hereby incorporated herein by reference.

FIELD

At least one embodiment of the invention generally relates to a method and/or a computer system for administration of medical applications executing in parallel.

BACKGROUND

Currently the development of computer-aided medical applications is not a standardized process. As a rule it consists of the analysis of the functionality needed by the user, the development of a corresponding technical concept and also implementation of the developed concept by executing a program.

Medical applications are characterized by a complex administration of a large number of internal states. The internal states generally reflect the information about user actions allowed, forbidden and executed in the UI (User Interface) of the application at a particular point. In addition the administration of the internal states of the application should take into account that the user can have a number of actions running in parallel and that the actions running in parallel can influence one another. The complex administration of the internal states of the application makes it difficult to expand it by additional components. These components should on the one hand be autonomous, generic and reusable. On the other hand the additional components are to participate in the states of the expanded application in order to meaningfully make use of its functionality within the application.

Consequently such applications result in problems such as for example restricted applicability or expandability or increased runtime, which is frequently only noticed at a late phase of development. Rectifying the problems demands considerable time and is also not cost-effective.

SUMMARY

In at least one embodiment of the invention, the above-mentioned process is improved, especially in respect of the above-mentioned characteristics.

One aspect of at least one embodiment of the invention is a method for administration of medical applications running in parallel, comprising:
  Creation of a number of application components as a result of beginning a number of user actions,
  Provision of a module for parallel execution and/or for coordination of the previously created application components.
  Provision of a least one communication interface for exchanging messages and/or data between an application component and a command of interest to the application component which has been initiated by one of the user actions,
  And removal of the application component created by the user action after ending the user action.

In accordance with at least one embodiment of the invention this enables internal, parallel application states of the medical applications and their configurable expansions with autonomous components to be administered at runtime, taking into account the internal, parallel application states.

Expediently an application component can select and/or request a command. The module for parallel execution and/or for coordination of the application components can forward a command which is of interest to the application component to the application component for processing. Furthermore this module can communicate the processing state of the application component to further locations involved. In such cases it can interrogate all application components currently running for accepted commands in order to give the user interface layer of the application the information necessary to put UI control components into the correct state.

A further aspect of at least one embodiment of the invention is a computer system for administration of medical applications running in parallel, comprising:
  At least one device/module for creating a number of application components initiated by a beginning of a number of user actions,
  A module for parallel execution and/or for the coordination of the previously created application components,
  At least one communication interface for exchange of messages and/or data between an application component and a command of interest to the application component which is able to be initiated by one of the user actions.
  And at least one device/module for removal of the application component created by a user action after ending of the user action The module for parallel execution and/or coordination of the application components can feature at least one sub-module for forwarding a command in which the application component is interested for processing to the application component.

A further aspect of at least one embodiment of the invention is a computer program product with computer program code for executing the method steps of at least one embodiment of the inventive method, with the computer program code being executed on a computer, especially on the above-mentioned computer system.

A further aspect of at least one embodiment of the invention is a computer program product of the type specified above, wherein the computer program code is stored on a medium able to be read by a computer.

At least one embodiment of the invention includes at least one of the following benefits:

At least one embodiment of the invention makes possible run-time expansions of the medical applications with autonomous components taking into consideration the internal, parallel application states. In such cases the applications have a layer architecture which bears the application components.

At least one embodiment of the invention simplifies application development by standardization. At least one embodiment of the inventive method is also generic and robust. It can be used for the development of any given medical applications.

BRIEF DESCRIPTION OF THE DRAWINGS

Described in greater detail below is an example embodiment of the invention which refers to a drawing.

The FIGURE shows:

A diagram of a typical communication between a parallel automaton and its environment. A so-called application backend and a plug-in component which can be characterized as an application component are shown in the FIGURE.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

An embodiment of the inventive method is based on the mechanism of a parallel automaton. It allows run-time expansions of the medical applications with autonomous components taking into account the internal, parallel application states. In this case the applications have a layer architecture which carries the application components.

In the parallel automaton PA user actions are mapped onto so-called commands or (input) commands e.g. Consume-Command. At the start of the user action a specific application component AK which is described in detail below is created (see CREATE_CENTERLINE for example) which is then removed at the end of the user action. The parallel automaton can execute any given number of application components in parallel and if required coordinate them with each other.

An application component can signal the commands in which it is interested and is not interested (e.g. AreYouInterested). The parallel automaton can interrogate all application components running on arrival of a command and forward the command for processing to interested application components. Furthermore the parallel automaton can interrogate all running application components for accepted commands in order to give the user interface layer of the application information which is required to place UI control components (also called UI controls) in the correct state (e.g. dim buttons etc.).

The application components are above all independent of each other.

The application component possesses the following properties:

1. At least one service adapter for making possible connectivity to 3rd-party medical systems, i.e. medical systems from OEMs.
2. At least one online/offline component which ensures that the application component can also deliver its respective services when a 3rd-party component is not available.
3. An ESB connectivity component which guarantees that the application component can be connected to the Enterprise Service Bus (ESB). As a rule the ESB covers a hospital department and therefore allows communication between the components/systems within the department.
4. A component for connecting the application component to the UI of the overall application which accommodates the application component.

5. The application component itself accommodates a least one medical domain framework and offers a suitable interface to the outside in order to guarantee high reusability of the application component in different medical applications.
6. There is at least one additional specific component for adaptability and expandability of the functionality of the application component. This also includes appropriate methods for adaptability and expandability of the application component.
7. There is a least one component which makes it possible for the application component to transparently use data from different data sources (so-called data cloud).
8. The capability of using the application component both in a workflow (standard case) and also standalone (without workflow) in a program.
9. In addition a connection of the instances of the proposed application component makes possible a workflow which implements an efficient medical data flow. Since large volumes of data are worked with in the medical area an efficient data flow such as for example a flow without unnecessary re-copying of the data is of great significance.
10. In addition the application component is able to suspend and resume its work if necessary. Such save points allow specific functionalities in the overall system to be disconnected and reconnected as required. This is especially useful in implementation of interruptible workflows (work can be resumed by a user other than the user who initiated the "suspend") and during resource administration.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for administration of medical applications running in parallel, comprising:
   creating a plurality of application components as a result of beginning a plurality of user actions;
   at least one of,
      executing, via a module, the created application components in parallel, and
      coordinating, via the module, the created application components;
   exchanging, via at least one communication interface, at least one of messages and data between a first application component and a command of interest to the first application component, which is initiated by one of the plurality of user actions, the module being executed by a processor; and
   removing and stopping the execution of the first application component created as a result of the user action, after ending of the user action.

2. The method as claimed in claim 1, wherein at least one of the command and a request is selectable via the first application component.

3. The method as claimed in claim 2, wherein the module is further useable to forward the command to the first application component for processing.

4. The method as claimed in claim 3, wherein the module is further useable to communicate processing states of the application components to further locations involved.

5. The method as claimed in claim 2, wherein the module is further useable to communicate processing states of the application components to further locations involved.

6. A non-transitory computer readable medium including program segments for, when executed on a computer device, causing the computer device to implement the method of claim 2.

7. The method as claimed in claim 1, wherein the module is further useable to forward the command to the first application component for processing.

8. The method as claimed in claim 7, wherein the module is further useable to communicate processing states of the application components to further locations involved.

9. The method as claimed in claim 1, wherein the module is further useable to communicate processing states of the application components to further locations involved.

10. A non-transitory computer readable medium comprising computer program code for executing the method of claim 1, upon the computer program code being executed on a computer.

11. A computer system for administration of medical applications running in parallel, comprising:
- at least one device to create a plurality of application components initiated by beginning a plurality of user actions;
- a processor configured to execute a module to at least one of,
  - execute the created application components in parallel, and
  - coordinate the created application components;
- at least one communication interface to exchange at least one of messages and data between a first application component and a command of interest to the first application component, which is initiateable by one of the user actions; and
- at least one device to remove and stop the execution of the first application component created by a user action after ending of the user action.

12. The computer system as claimed in claim 11, wherein the module includes at least one sub-module to forward the command to the first application component for processing.

* * * * *